United States Patent [19]
Ryan et al.

[11] Patent Number: 5,067,945
[45] Date of Patent: * Nov. 26, 1991

[54] SAFETY NEEDLED MEDICAL DEVICES CAPABLE OF ONE-HANDED MANIPULATION

[75] Inventors: Dana W. Ryan, Franklin; James M. Kaiser; Robert M. Hinsch, both of Brentwood, all of Tenn.

[73] Assignee: Ryan Medical, Inc., Brentwood, Tenn.

[*] Notice: The portion of the term of this patent subsequent to May 8, 2007 has been disclaimed.

[21] Appl. No.: 303,588

[22] Filed: Jan. 27, 1989

Related U.S. Application Data

[63] Continuation-in-part of Ser. No. 162,569, Mar. 1, 1988, and a continuation-in-part of Ser. No. 224,920, Jul. 27, 1988, Pat. No. 4,923,445.

[51] Int. Cl.$^5$ ............................................. A61M 5/32
[52] U.S. Cl. .................................... 604/198; 601/283; 601/199; 128/763
[58] Field of Search ............... 604/110, 192, 194, 195, 604/196, 197, 198, 240–243, 263, 111, 181, 185, 18, 188, 199, 211, 212, 214, 216, 232, 234; 128/760, 762–767, 770

[56] References Cited

U.S. PATENT DOCUMENTS

| | | | |
|---|---|---|---|
| 2,571,653 | 10/1951 | Bastien | 601/198 |
| 2,740,404 | 1/1956 | Kohl | 604/198 |
| 3,073,306 | 1/1963 | Linder | 601/198 |
| 3,356,089 | 12/1967 | Francis | 604/197 |
| 3,469,581 | 9/1969 | Burke | 604/243 |
| 3,487,834 | 1/1976 | Smith, Jr. et al. | 604/197 |
| 3,890,971 | 6/1975 | Leeson et al. | 604/198 X |
| 3,930,499 | 1/1976 | Rimbaud | 604/227 |
| 3,969,581 | 9/1969 | Burke | 601/243 |
| 4,031,077 | 12/1966 | Mitchell | 601/198 |
| 4,140,127 | 2/1979 | Cianci et al. | 604/171 |
| 4,168,699 | 9/1979 | Hausor | 604/171 |
| 4,170,993 | 10/1979 | Alvarez | 601/198 |
| 4,186,745 | 2/1980 | Lewis et al. | 604/265 |
| 4,356,822 | 11/1952 | Winstead et al. | 604/198 |
| 4,383,530 | 5/1983 | Bruno | 604/274 |
| 4,411,656 | 10/1983 | Cornett, III | 604/263 |
| 4,417,887 | 11/1983 | Koshi | 604/192 |
| 4,425,120 | 1/1954 | Sampson et al. | 604/198 |
| 4,568,336 | 2/1986 | Cooper | 604/240 |
| 4,573,976 | 3/1956 | Sampson et al. | 604/263 |
| 4,613,326 | 9/1986 | Szwarc | 604/218 |
| 4,643,199 | 2/1987 | Jennings et al. | 604/198 |

(List continued on next page.)

*Primary Examiner*—Randall L. Green
*Assistant Examiner*—K. Reichle
*Attorney, Agent, or Firm*—David P. Gordon

[57] ABSTRACT

Improved shielded medical devices which minimize accidental needlesticks of the skin by an exposed contaminated needle are provided. The medical devices include a hollow inner tube body and a telescoping outer shield. The outer surface of the inner tube has front and rear circumferential grooves, with a shoulder located forward of the front groove and a ramp located rearward of the front groove and decreasing in diameter as it extends away from the front groove. The shoulder has a larger diameter than the ramp diameter adjacent the front groove and permits the shield to be slided over the inner tube without locking into the inner tube during assembly. The outer shield has two inwardly extending circumferential protrusions in proximate location to each other, and at least one outwardly extending gripping flange. A first of the protrusions is located at the rear end of the shield and yieldingly engages the rear groove during use of the medical device, thereby permitting normal use of an exposed needle. After needle contamination, the shield is gripped by the thumb and forefinger of the practitioner and slid forward along the inner tube until the forwrd inwardly extending protrusion of the shield slides up the ramp and lockingly engages the front groove. The shield is then locked relative to the inner tube such that the needle is shielded. With properly arranged gripping flanges, the shielding action may be accomplished with one hand.

38 Claims, 4 Drawing Sheets

U.S. PATENT DOCUMENTS

| | | | |
|---|---|---|---|
| 4,655,751 | 4/1987 | Harbaugh | 604/198 |
| 4,666,435 | 5/1987 | Braginet | 604/198 |
| 4,681,567 | 7/1982 | Masters et al. | 604/198 |
| 4,702,738 | 10/1957 | Spencer | 604/198 |
| 4,702,739 | 10/1987 | Milcrad | 604/198 |
| 4,723,943 | 2/1988 | Spencer | 604/198 |
| 4,737,144 | 4/1988 | Choksi | 604/198 |
| 4,738,603 | 4/1988 | Beyan | 604/198 |
| 4,747,830 | 5/1988 | Glayer et al. | 604/110 |
| 4,747,837 | 5/1988 | Hauck | 604/263 |
| 4,758,231 | 7/1988 | Haber et al. | 604/198 |
| 4,790,827 | 12/1988 | Haber et al. | 601/198 |
| 4,816,022 | 3/1989 | Poncy | 604/198 |
| 4,820,282 | 1/1989 | Hogan | 604/177 |
| 4,834,711 | 5/1989 | Greenfield | 604/172 |
| 4,838,876 | 6/1989 | Wong et al. | 604/265 |
| 4,865,592 | 9/1989 | Ryeroft | 604/197 |
| 4,871,355 | 10/1989 | Kikkawa | 604/198 |
| 4,917,679 | 4/1990 | Kronner | 604/198 |
| 4,923,445 | 5/1990 | Ryan | 604/198 |

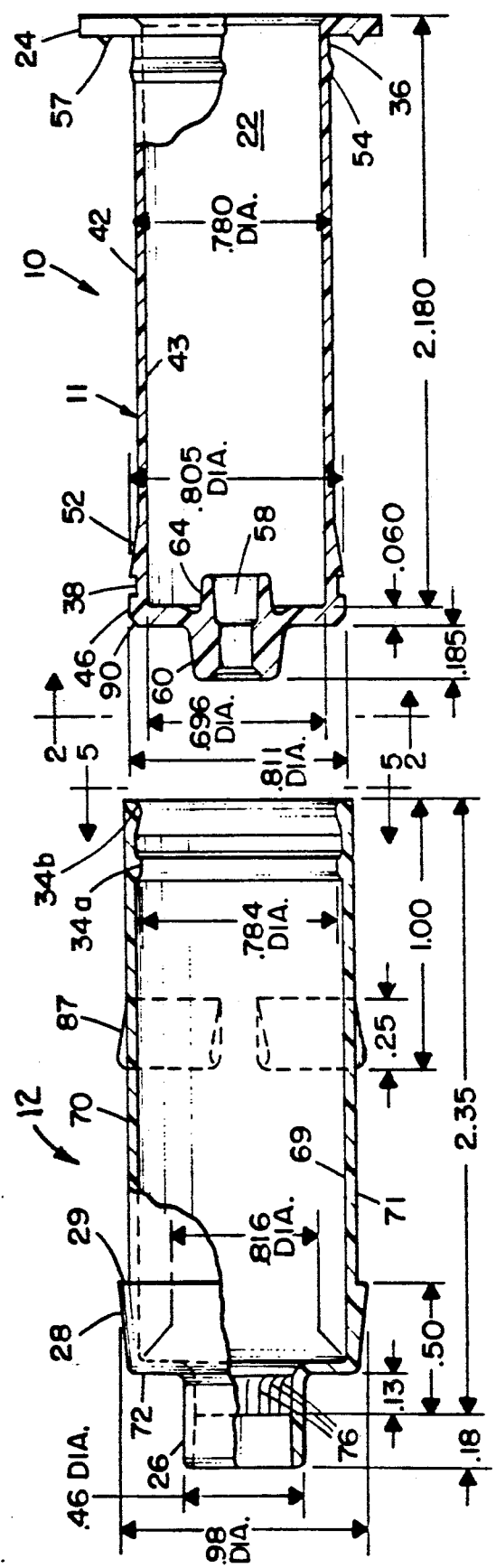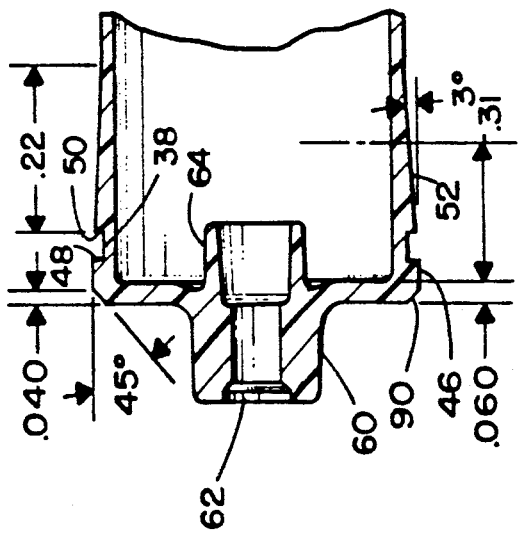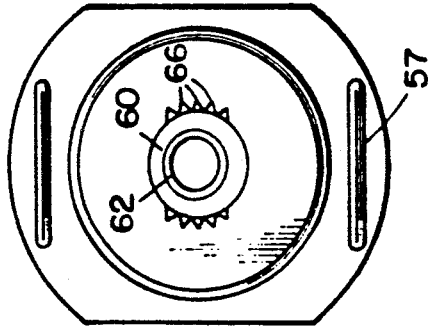
FIG. 1.
FIG. 3.
FIG. 2.

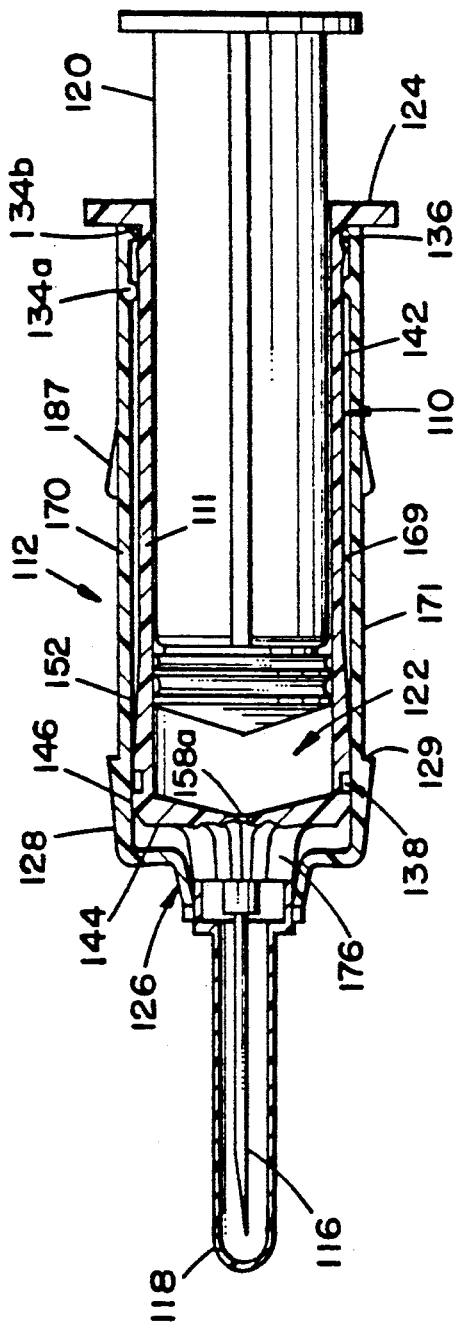

SAFETY NEEDLED MEDICAL DEVICES CAPABLE OF ONE-HANDED MANIPULATION

This application is a continuation-in-part of Ser. No. 162,569, filed Mar. 1, 1988, and of Ser. No. 224,920, filed July 27, 1988, now U.S. Pat. No. 4,973,445, both of which are hereby incorporated by reference herein.

BACKGROUND OF THE INVENTION

The present invention generally relates to improvements in safety needled medical devices which are designed to minimize the incidence of accidental pricking of the skin and resulting spread of infectious diseases by an exposed contaminated needle after use thereof. The disclosed devices may be used as blood collection tube holders, syringes with or without an attached needle, prefilled syringes, and IV catheters.

Accidental needlesticks have long been a problem in the medical profession. Accidental needlesticks most often occur during the recapping of a contaminated needle or immediately after use and prior to safe disposal. Such needlesticks place the medical professional (clinician) at risk. When needles are not recapped, additional accidental needlesticks are caused by uncapped needles found in patient beds, linens, and in garbage cans, and place health care housekeeping and sanitation personnel at risk. Because accidental needlesticks can now result in deadly incurable diseases as well as the previously appreciated serious, but usually curable diseases, the need for eliminating the needlestick problem has reached extreme urgency. In addressing the urgency, many devices have been proposed. Indeed, the prior art discloses a number of devices which are arranged to shield the needle of the device after use, but none are as simple to manufacture, assemble, an use as the devices of the present invention. A benefit of the devices of the present invention is that the devices require no change in the method of use or technique by medical personnel, i.e. the medical practioners will use the devices in the same way they previously used standard hypodermic syringes, blood collection tube holders, etc., except that after use they will move a shield to cover the exposed contaminated needle in a very easy, simple, and straightforward manner, requiring the use of only one hand.

Included in the prior art among many safety devices are safety-needled syringes such as are disclosed in U.S. Pat. Nos. 2,571,653 to Bastien, 4,026,287 to Haller, 4,425,120 to Sampson et al., 4,573,976 to Sampson et al., 4,631,057 to Mitchell, 4,643,199 to Jennings, Jr. et al., 4,655,751 to Harbaugh, 4,666,435 to Braginetz, 4,681,567 to Masters et al., 4,702,738 to Spencer, 4,702,739 to Milorad, 4,723,943 to Spencer, 4,737,144 to Choksi, 4,738,603 to Bogan, 4,747,830 to Gloyer et al, 4,747,837 to Hauck, and 4,758,231 to Haber et al. None of these devices, however, have yet gained acceptance in the medical field. Many of the devices require complex pieces or are of such a design such that they are expensive to manufacture and assemble. Others of the devices require the clinician's procedure and technique to change. Yet other devices, while relatively simple in construction and use, do not provide the required level of safety desirable from a "safety" needled device.

SUMMARY OF THE INVENTION

It is therefore an object of the present invention to provide improved shielded medical devices which are easy and economical to manufacture and assemble, which do not require change of technique and procedure to use, and which may be manipulated in one hand by a medical practitioner.

A further object of the present invention is to provide improved shielded medical blood collection tube holders, and syringes of different kinds with standardized locking mechanisms in which movement of the shield from the unshielded position to the locked shielded position may be accomplished in an easy, uniform sliding motion requiring the use of a single hand.

Another object of the invention is to provide economical improved shielded medical devices utilizing a shield which provides a positive indication when locking into a shielded position.

Yet another object of the present invention is to provide improved shielded medical devices in which rotation of the shield relative to an inner tube body is prevented when the medical device is in use.

The improved safety needled medical devices of the present invention achieve the above-listed objects as hereinafter disclosed. The devices, whether for use with syringes or blood collection tube holders, are comprised of two telescoping parts: an inner tube body and an outer safety shield. The inner tube body (hereinafter referred to as the "tube", or the "inner tube") is hollow and generally cylindrical and is adapted to have mounted at its forward end a standard hollow needle, and to receive a standard plunger or vacuum blood collection tube through its open rearward end. The outside of the inner tube is configured with at least two axially spaced circumferential grooves with one of the grooves preferably being formed towards the rearmost end of the tube adjacent an outward extending finger positioning flange, and at least one other groove preferably being near the forward end of the tube. The rearmost groove is basically a ramp which decreases in diameter as it extends rearward. From the top of the ramp towards the front groove, the outer surface of the inner tube first decreases in diameter, levels off, and then increases in diameter (forming a second ramp) until terminating in the front groove. Thus, a valley is formed between two ramps. Adjacently forward the front groove is a shoulder of slightly greater diameter than the diameter of the outer surface adjacently rearward of the front groove.

The outer safety shield (hereinafter referred to as the "shield", or the "outer shield") is of slightly larger diameter than the inner tube (including very slightly larger than the front shoulder), and is arranged to be slidable relative to the inner tube. The outer shield preferably includes two circumferential inward protrusions in relative close proximity one to the other toward the rear end of the outer shield. The protrusions have an inner diameter approximately equal to the outer diameter of the valley of the inner tube. The rearward of the two protrusions is arranged to engage the rear groove of the inner tube when the shield is in a non-shielded retracted position, while the forward of the two protrusions engages the forward groove of the inner tube when the shield is slid forward into a shielding position. The shield then prevents accidental contact with the contaminated needle, and the rearward protrusion of the outer shield acts both to stabilize the shield relative to the inner tube so that the shield cannot be removed, and also as a second safety catch should the user manage to force the first protrusion forwardly out of the locking groove. Ratchet, or other similar means connected with the inner tube and the outer shield are provided to prevent rotation of the outer shield relative to the inner tube when the shield is in its retracted position and the needle is exposed. The shield also includes ramped flanges on its outer surface around the middle portion of the shield. The ramps increase in diameter as they extend forward along the outer surface of the shield and provide a pushing and gripping surface (of opposite direction to the rear flange of the inner tube) for permitting a one-handed manipulation of the medical devices to accomplish shielding.

A better understanding of the improved safety needle medical devices of the present invention, and additional advantages and objects of the invention will become apparent to those skilled in the art upon reference to the detailed description and accompanying drawings.

BRIEF DESCRIPTION OF THE DRAWINGS

FIG. 1 is a partially broken-away plan view showing the inner tube and outer shield of the invention prior to assembly for use as a medical safety-needled phlebotomy device;

FIG. 2 is an front end view of the inner tube of FIG. 1, taken along line 2—2 of FIG. 1 and showing a ratchet mechanism and a rear flange;

FIG. 3 is an enlarged partial cross-sectional view of the front ramp, front groove, shoulder section of the inner tube;

FIGS. 8A and 8B are partially broken-away plan views showing the inner tube and outer shield of the safety needled syringe invention in the unshielded and shielded and positions respectively;

DETAILED DESCRIPTION OF THE PREFERRED EMBODIMENT

Figure 4:
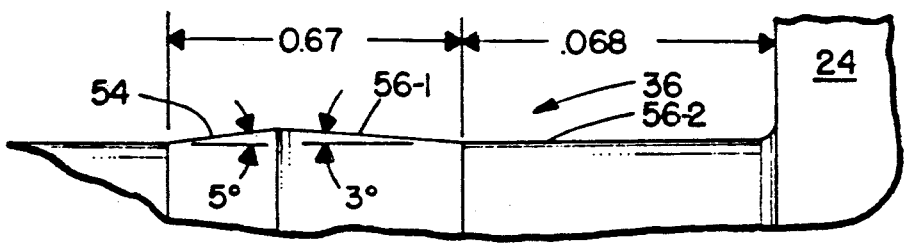
FIG. 4 is an enlarged partial cross-section view of the rear ramp, rear groove, rear flange section of the inner tube.

FIGS. 1–7 generally show the basic structure of the improved safety needled device of the invention although they are particularly directed to a blood collection tube holder. FIGS. 8A and 8B and FIGS. 9A and 9B are directed to the syringe and prefilled syringe embodiments respectively, while FIG. 10 shows a second embodiment of the basic structure.

Referring to FIGS. 1–7, the improved safety medical device is seen comprising two generally cylindrical pieces: a hollow inner tube 10 and a hollow outer shield 12. Both pieces are preferably formed via injection molding of polypropylene, although other materials of similar properties could be utilized. Looking at detail at the inner tube 10 as is best seen in FIGS. 1–4, the inner surface 43 of the tube is of approximately 0.696 inch diameter along its entire length to provide a cavity 22 which can accommodate a standard blood collection vacuum tube (not shown). The outer surface 42 of the tube 10 along its central portion 11 is of approximately 0.780 inch diameter (approximately the same diameter as the inner surface of the protrusions of the outer shield 12). As best seen in FIG. 3, at the forward end of the outer surface 42 of tube 10, a ramp 52 of an approximately three degree angle is formed. When the ramp 52 terminates at forward groove 38 which is bounded by forward ledge 48 and rear ledge 50, its outer diameter is approximately 0.805 inches. Directly forward of front groove 38 is a shoulder 46 which must be of slightly greater diameter than the diameter of ramp 52 at its forward termination point. Thus, as shown, the diameter of shoulder 46 is approximately 0.811 inches. As will be described hereinafter, it is critical that the diameter of shoulder 46 be greater than the diameter of ramp 52 at its forward termination point. It is also strongly preferred that the diameter of shoulder 46 at the same time be smaller than the general inner diameter of the outer shield 12. Since the inner diameter of the provided outer shield is approximately 0.816 inches, the shoulder 46 is preferably no greater than 0.815 inches in diameter. As best seen in FIG. 3, the front end 90 of shoulder 46 is rounded and angled to permit a more expeditious loading of the outer shield 12 onto the inner tube 10 during assembly, as will be described in more detail hereinafter.

Turning to FIG. 4, the outer surface 42 of the rearward end of inner tube 10 is seen in more detail. At the rearward end of the outer surface 42 of tube 10, a very short ramp 54 of an approximately five degree angle is formed which increases diameter as it extends rearwardly. When the ramp 54 terminates at rearward "groove" 36 its outer diameter is approximately 0.787 inches. Rearward "groove" 36 then basically comprises a ramp 56-1 at an approximately three degree angle and of decreasing diameter until a 0.780 diameter surface is attained, and a small flat portion 56-2. The rear "groove" is defined by the start of ramp 56-2 and a rear flange 24 which has gripping tines 57 (seen in FIG. 1). As will be described hereinafter, groove 36 serves to keep the outer sleeve 12 in a retracted position to permit blood extraction or fluid injection.

Other aspects of inner tube 10 in the blood collection embodiment of FIGS. 1–4, include a forwardly extending cylindrical wall 60, a rearwardly extending cylindrical wall 64, and a ratchet means 66. The forwardly extending wall 60 is provided on its inside circumference with threads 62 or other means by which a standard hollow blood collection needle may be attached so as to communicate through annular opening 58 with cavity 22. Reardwardly extending cylindrical wall 64 is coaxial with the inner tube wall 43 and extending rearwardly from the forward section of the inner tube 10. Cylindrical wall 64 is shaped to receive the forward end of a vacuum blood collection vial (not shown) to provide a sealed engagement therebetween. Ratchet means 66, as best seen in FIG. 2, comprises a plurality of teeth which extend radially outwardly from cylindrical wall 60. Five teeth 66 are shown on diametrically opposed sides of wall 60, but the exact number and exact location of the teeth 66 may be varied. As will be described hereinafter, teeth 66 mesh with reciprocating notches on the shield 12 to prevent rotation of shield 12 relative to inner tube 10 when the shield is in its retracted position.

The outer shield 12 is seen best in FIGS. 1, and 5-7. The outer shield 12 is basically comprised of cylindrical wall 70 having inner surface 69 and outer surface 71. With an inner tube 10 having a front shoulder of outer diameter 0.811 inches, the diameter of the outer shield inner surface 69 is preferably 0.816 inches. In fact, the inner diameter of the outer shield 12 preferably is always greater than the largest diameter of any part of inner tube 10.

Figure 6:
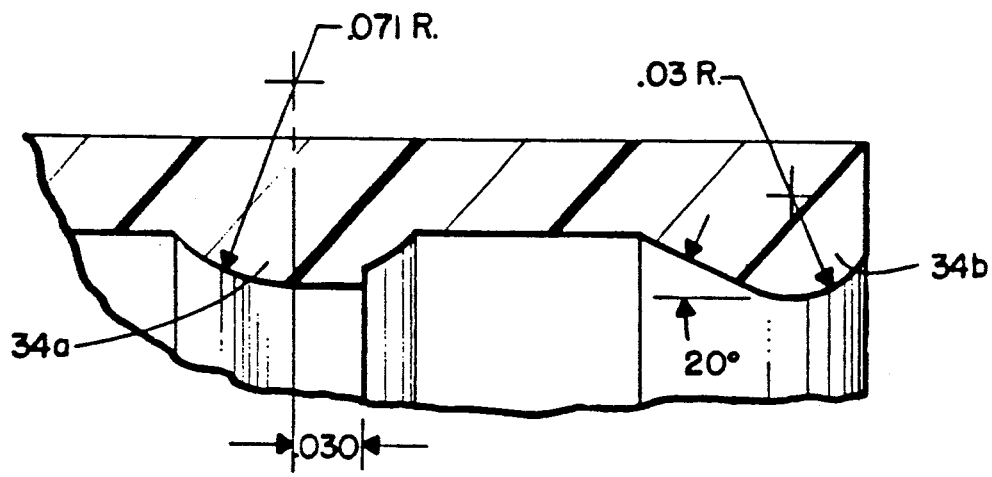
FIG. 6 is an enlarged partial cross-sectional view of protrusions at the rear end of the outer shield.

As best seen in FIGS. 1 and 6, extending inwardly from cylindrical wall 70 at the rearward end are circumferential protrusions 34a and 34b. While a single protrusion could be utilized, as will be described hereinafter, the use of two protrusions provides advantages. Protrusions 34a and 34b are preferably uninterrupted, although as seen in FIG. 10, one or both of the protrusions may be divided into a plurality of lugs. Protrusion 34b is arranged to keep shield 12 in a retracted position during use of the needled assembly. Thus, protrusion 34b is arranged to sit in groove 36 of the inner tube 10, and is provided with an approximate inner diameter of 0.780 inches which is equal to the outer diameter of groove 36 and valley 11. To permit protrusion 34b to be relatively easily unseated from groove 36 during shielding, protrusion 34b is tapered and rounded as shown. Protrusion 34a is slightly smaller than protrusion 34b (i.e. its approximate inner diameter is 0.784 inches), and has a rounded forward end and a sheared rear end which provide a locking ledge as will be described in more detail hereinafter.

At the forward end of outer shield 12 an end wall 72 is provided with annular locking nozzle 26 extending therefrom. Besides supporting inwardly extending ratchet means or teeth 76 which are arranged to engage the locking teeth 66 of the inner tube 10 as will be described hereinafter, locking nozzle 26 provides guidance during needle attachment and an additional margin of safety against blood leakage and from the needle itself.

Figure 7:
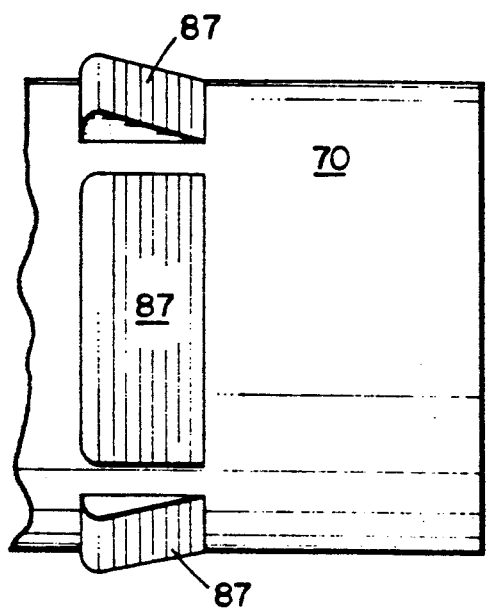
FIG. 7 is an elevational view of the gripping ramps on the outer surface of the outer shield.
Figure 5:
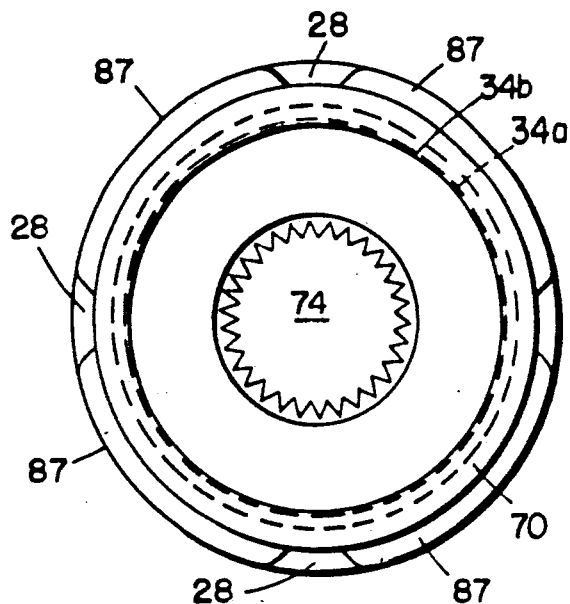
FIG. 5 is a rear end view of the outer shield of FIG. 1, taken along line 5—5 of FIG. 1 and showing a ratchet mechanism and gripping ramps.

Turning to FIGS. 5 and 7, details of the outer surface of outer shield 12 are shown. Provided around the midportion of cylindrical wall 70 are ramped flanges 87 which increase in diameter as they extend forward along the outer surface 71 of the shield 12. Ramped flanges 87 provide a pushing and gripping surface for permitting a one-handed manipulation of the medical device as will be described hereinafter. Also formed near the forward end of outer shield 12 on the outer surface thereof is a flange 28 which ramps in the opposite directed to flanges 87. Flange 28 provides a safety ridge or back face 29 to prevent the sliding of the practitioner's hands during use. Also, flange 28 provides a gripping surface for a two-handed manipulation of the medical device.

FIGS. 8A and 8B show the safety-needled medical device invention in its syringe embodiment with the shield in its retracted (unshielding) and extended (shielded) positions respectively. In FIGS. 8A and 8B, parts which are identical to or similar to parts of the phlebotomy device of FIGS. 1-7 are notated by numbers greater by one hundred than the notations of FIGS. 1-7. Additionally shown in FIGS. 8A and 8B are the needle assembly 116 which is screwed into the inner tube 110, a needle guard 118 which is removed prior to injection, graduated markings 140 (typically in cc measurements) which may be located on either the inner shield or outer tube as desired, and a plunger 120. Plunger 120 is used for either forcing the contents of chamber 122 through a small annular opening 158a and into and through needle 116, or to aspirate a fluid through needle 116, annular opening 158a, and into chamber 22. Annular opening 158a is somewhat different than opening 58 of FIG. 1 because annular opening 58 is arranged to receive the vacuum tube as well as connect a needle assembly to chamber 22, while annular opening 158a is a needle sized opening.

As indicated in FIG. 8A, prior to use of the medical device, needle cap 118 is located over needle 116. In order to give an injection, the cap is removed, the needle is placed in a medicinal container, plunger 120 is drawn backwards to aspirate the medicine, the needle is injected into the patient, and the plunger is pushed forward. During all these procedures, rear projection 134b is seated in rear groove 136 to prevent forward movement of shield 112 relative to inner tube 110, and teeth 166 are meshed with ratchet mechanism 176 to prevent rotational movement of shield 112 relative to inner tube 110. After injection, the needle is removed from the patient, and the shield is extended into its locked shielding position, as will be discussed hereinafter. In the shielding position, protrusion 134a is fixedly seated in front groove 138 while protrusion 134b engages ramp 152.

Figure 9A:
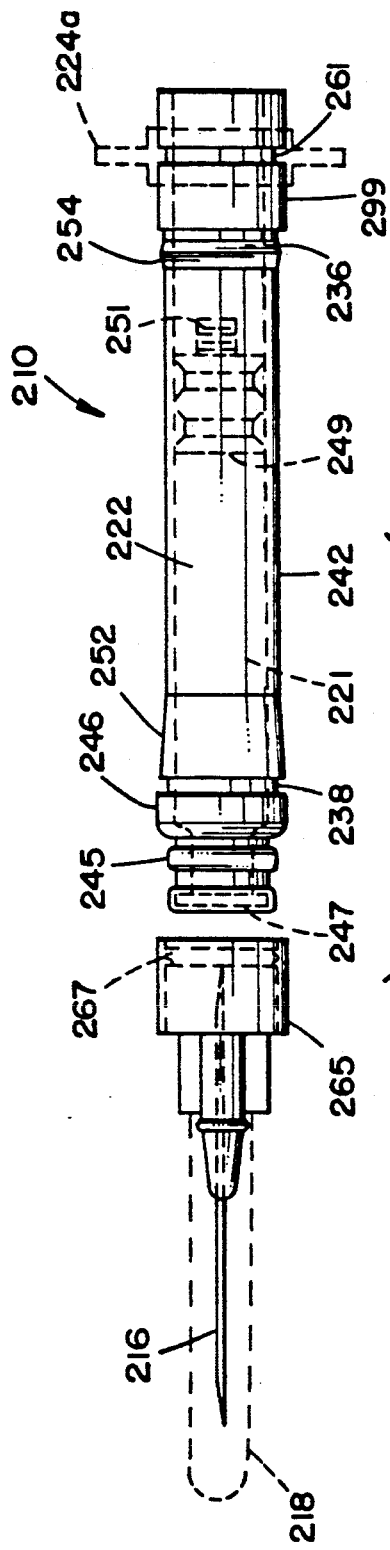
FIG. 9A is a plan view of of the inner tube for a prefilled syringe embodiment of the safety needled invention.
Figure 9B:
FIG. 9B is a plan view of the plunger arm for a prefilled syringe.
Figure 10:
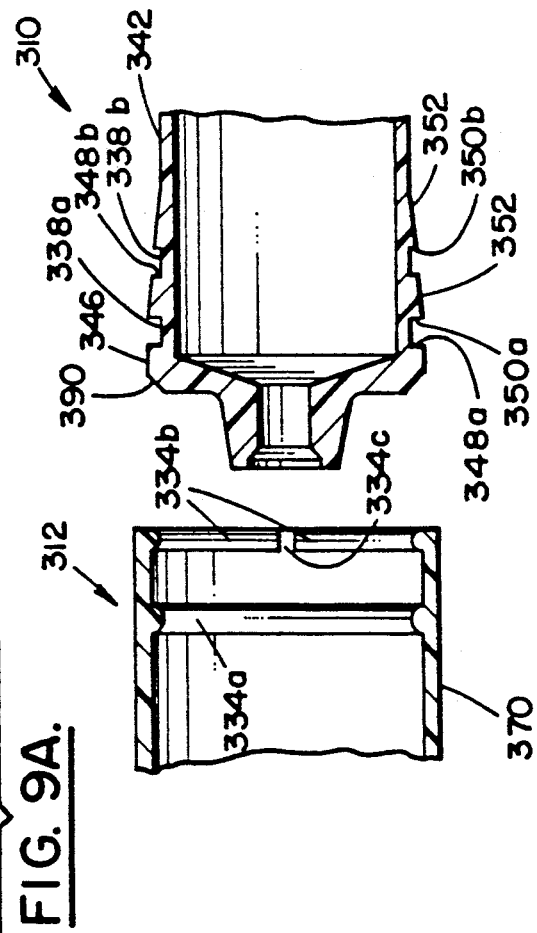
FIG. 10 is a plan view of the front of the inner tube, and the rear of the outer shield of a second embodiment of the safety needled invention.

The inner tube 210 of the prefilled safety syringe embodiment of the invention is seen in FIG. 9A. (In this embodiment corresponding elements will have numbers corresponding to those of FIG. 1, with the numbers of FIG. 9A being greater by two hundred). The inner tube 210 combines many of the standard features of a prefilled syringe with the afore-described inner tube features of the instant safety needled invention. Thus, for purposes of the standard prefilled syringe, the inner tube 210 is preferably made of or lined with glass. The medicated liquid 221 is maintained in chamber 222 which is bounded by cylindrical wall 242, a shaped metal cap 245 having a hermetic seal 247, and a rubber plunger seal 249 having a male threaded member 251 extending therefrom. Also, for purposes of the standard prefilled syringe, the rear end 299 of the inner tube 210 is provided with a groove 261 for a preferably plastic snap-on flange 224a, while the front end metal cap 245 is arranged to mate with a needle hub 265 having a ridge ring 267 on one end for mating with the metal cap 145 and means for accepting and holding a double pointed needle 216 on the other end. Typically, the needle 216 is provided with a protective cover 218 which must be removed before an injection. A disposable plunger arm 205 seen in FIG. 9B is provided with a female thread member 281 which is screwed onto the male threaded member 251 of the inner tube 210 prior to injection. After mating, force may be applied to the plunger arm 205 so as to force the medicated liquid out through the double pointed needle 216.

As seen in FIG. 9A, the inner tube 210 also includes the safety-needled features. Thus, provided in the outer surface of the inner tube 210 are front and rear grooves 238 and 236 into which the protrusions of an outer shield may extend. Also, the outer surface of inner tube 210 is provided with front shoulder 246, front ramp 252, and rear ramp 254. An outer shield for the prefilled syringe embodiment (not shown) would essentially take the form of shield 12 of FIG. 1.

Turning to FIG. 10 (where elements corresponding to FIG. 1 are denoted by numbers three hundred removed therefrom), additional embodiments of the invention are seen which are applicable to the vacuum tube (phlebotomy) and syringe embodiments. Thus, the rear end of shield 312 is shown with two protrusions 334a and 334b, except that protrusion 334b is segmented by spaces 334c. If desired, either or both of protrusions 334a and 334b can be so segmented. Also, if desired, protrusions 334a and/or 334b could be segmented by providing an incisions or slots (not shown) in the rear of outer shield 312. Also, as seen in FIG. 10, the inner tube is provided with two front grooves 338a and 338b into which protrusions 334a and 334b may extend. With two front grooves, preferably groove 338a is of a slightly greater width than groove 338b, while protrusion 334a has a slightly greater width than protrusion 334b (and groove 338b). In this manner, during the shielding action, when protrusions 334b of shield 312 are unseated from their rear groove and the shield is moved forward, protrusion 334a will not engage in groove 338b. Rather, protrusion 334a will engage groove 338a, while protrusion 334b will engage groove 338b. Such a double lock could provide additional stability to the apparatus and added security against the shield being moved forward and off the inner tube 310.

In manufacturing the safety needled medical device of the invention, the inner tube (except for the prefilled syringe embodiment) and the outer shield are molded out of polypropylene plastic or materials of similar properties. For assembly (for brevity, reference will only be had to the embodiment of FIG. 1), the inner tube is then preferably placed upright with its rear end flush with a horizontal surface and some means projecting into the cavity 22 to hold the inner tube upright. The outer shield 12 is correspondingly arranged, except that the outer shield is held from the outside and above the inner tube 10. Preferably, just prior to forcing outer shield 12 onto inner tube 10, the outer shield 12 is lowered such that protrusion 34b of outer shield 12 engages the angled front 90 of shoulder 46 and centers the shield 12 relative to inner tube 10. Then, in a sharp downward motion, outer shield 12 is loaded onto inner tube 10. The sharp downward motion forces protrusions 34b and 34a respectively over shoulder 46 of inner tube 10, thereby instantaneously expanding the resilient shield 12 at the protrusion locations of its rear end. Before the shield 12 can reassume its unstressed position, each protrusion has passed over and by groove 38 and onto ramp 52 of inner tube 10. However, because of the outer shield's resilient nature, as the protrusions pass groove 38 they do contract somewhat. Thus, ramp 52 must be provided with a smaller outer diameter than shoulder 46, so that the protrusions will not be nicked or even sheared off in the process. As the shield is further pushed downward over the inner tube, the protrusions slide down ramp 52 and long valley 11. Rear protrusion 34b then rides up ramp 54 and into groove 36 to assume the fully assembled position, while protrusion 34a rests along ramp 54 or on valley 11. In the fully assembled position, the outwardly extending ratchet teeth 66 of inner tube 10 engage the ratchet teeth 76 of outer tube 12 to prevent rotation of the shield 12 relative to the inner tube 10.

The so-assembled safety medical device may then be used in numerous circumstances and for differing purposes, all of which are within the scope of this invention. A common use would be by a clinician for obtaining blood samples from a patient. For this usage, the clinician screws a capped sterile blood collection needle assembly (similar to that shown in FIG. 9A) into the threads 62 of inner tube 10. Typically, the phlebotomy needle is pointed on both ends and extends a short distance into cavity 22 of inner tube 10. A vacuum vial (not shown) having a rubber or plastic stopper is then inserted into the tube 10. The stopper of the vacuum vial is penetrated by contact with the rearward extension of the needle, and blood is drawn into the vacuum vial through the needle which has been inserted into a vein of the patient. Once the blood sample is taken (if desired, several tubes of blood may be obtained), the needle is removed from the patient and the vacuum vial(s) now filled with blood is removed from the inner tube 10. The contaminated needle is then shielded by using either a one or two handed method. In the one-handed method, the practitioner might place one or two fingers behind the rear flange 24 of the inner tube, two or three fingers on the shield surface, and the thumb opposite the two or three fingers on the shield surface. Pushing with the thumb, and if desired with additional fingers on either the ramped flange 87, the safety flange 28 or on the outer surface 71 of outer shield 12, the rear protrusion 34b is unseated from rear groove 36 and the shield is slid forward relative to the inner tube 10 with the protrusions 34 riding along valley 11 of outer shield 12. When protrusion 34a reaches ramp 52, resistance to the sliding of the shield is met. The practitioner may then move all fingers forwards of rear flange 24, and typically using the thumb and forefinger may press forward on the ramped flange 87 or safety flange 28 so as to force protrusion 34a up ramp 52 and into front groove 38. As the protrusion 34a goes into front groove 38, a click or snap is typically audible. With protrusion 34a engaged in front groove 38, shield 12 completely envelops the needle (in a manner seen in FIG. 8B), thereby rendering it harmless.

In order to permit an easy one-handed manipulation of the safety needled device, the plastic used in the molding process is preferably mixed with a small amount of lubricant (e.g. 0.25-0.5% in weight). The lubricant included in the resulting molded tube and shield not only eases the practitioner's task of sliding the protrusion of the shield up the ramp and into the circumferential groove, but helps in the molding process by expediting removal of parts from the mold. While a preferred lubricant is a highly purified nitrogenous aliphatic compound, other lubricants can be utilized. Also, a small amount of polyolefin clarifier and colorant can be added to the plastic if so desired to provide a clear tint to the naturally translucent plastic.

In the two-handed technique, the rear flange 24 of inner tube 10 is held typically by the forefinger and either the thumb or third finger of one hand, and the shield 12 is held at the ramped flange 87, the safety flange 28 or on the outer surface 71 by the other hand. Then, either by pulling on rear flange 24, pushing on shield 12, or a combination of both, the shield 12 is slid along valley 11, and the protrusion 34a is slid over ramp 54 until it snaps or clicks into front groove 38.

Regardless of the technique used to engage the shield protrusions 34a with the inner tube groove 38 (and regardless of the embodiment; i.e. FIGS. 1-7, FIGS. 8A and 8B; FIGS. 9A and 9B, etc.) it is thereafter extremely difficult to remove the shield from the inner tube. Once protrusion 34a is locked into circumferential groove 38, the front shoulder 46 on the inner tube 10 prevents movement of the shield 12 forward, and the forward edge of ramp 52 acts as a second shoulder for preventing movement of the shield backward. Also, the shaped nature of the rear edge of forward protrusion is useful in helping stop rearward movement of the shield.

Further, the second protrusion 34*b* acts to stabilize the assembly and provide an added measure of safety should protrusion 34*a* somehow become unseated from groove 38 and be moved forward. Thus, with the provided shield and inner tube, a positive lock is assured, completely protecting medical personnel and others against needlestick injuries from contaminated needles. The shielded medical device may then be safely discarded in accord with established procedures.

There has been described and illustrated herein various improved shielded safety medical devices. While particular embodiments of the invention have been described, it is not intended that the invention be limited thereby, as it is intended that the invention be broad in scope. Thus, while particular measurements for the inner tube and shield of the safety phlebotomy device were provided, it will be appreciated that different sized phlebotomy and syringe devices can be made within the scope of the invention, provided of course that the shoulder located forwardly adjacent the front groove is larger than the diameter of the ramp rearwardly adjacent the front groove, and preferably just slightly smaller than the inner diameter of the shield, and provided that the inner protrusions on the shield are smaller than the shoulder and preferably smaller than the front ramp diameter. Therefore, it will be apparent to those skilled in the art that yet other changes and modifications may be made to the invention as described without departing from the spirit and scope of the invention as so claimed.

I claim:

1. A medical device for assembly with a hollow needle, comprising:

a) an inner tube member having a substantially cylindrical inner surface, a front end having means for securing the hollow needle thereto, an open rear end, an outwardly extending first gripping flange substantially at said open rear end, and an outer surface having first and second substantially circumferential grooves, said first groove being forward of said second groove, said outer surface having a shoulder adjacently forward of said first groove with said shoulder being slightly larger in diameter than the outer surface of said inner tube member adjacently rearward of said first groove; and b) a plastic hollow outer shield member having a substantially cylindrical outer surface having at least one second gripping flange extending outwardly therefrom, and an inner surface with an inner diameter slightly larger than the outer diameter of at least most of said outer surface of said inner tube member, a front end having an opening therein, a substantially open rear end, and at least one inwardly extending protrusion located along the inner surface of said plastic hollow outer shield member, said at least one inwardly extending protrusion for engaging at least one of said first groove and said second groove such that when said at least one inwardly extending portusion engages said second groove, said shield member is maintained in a first retracted position, and when said at least one inwardly extending protrusion engages said first groove, said shield member is locked in a second extended position in which the needle is protected by said shield member, wherein said at least one inwardly extending protrusion, engaging said second groove is disengageable from said second circumferential groove by application of reverse axial forces on said first and second gripping flanges, and said shield member is slidable between said first position and said second position, and the inner diameter of said at least one inwardly extending protrusion when engaging said first groove is smaller than the outer diameter of said shoulder and smaller than the outer diameter of said outer surface of said inner tube member directly rearwardly adjacent said first groove, and in an assembly mode, said at least one inwardly extending protrusion of said outer shield member engages said shoulder of said outer surface of said inner tube member and flexes outwardly as a result of the engagement, and engages said outer surface of said inner tube member rearward of said first groove without fixedly engaging said first groove.

2. A medical device according to claim 1, wherein:
said outer surface of said inner tube member includes a first ramp substantially rearwardly adjacent said first groove, said first ramp being of decreasing diameter as it extends away from said first groove.

3. A medical device according to claim 2, wherein:
said outer surface of said inner tube member further includes a second ramp substantially forwardly adjacent said second groove, said second ramp being of decreasing diameter as it extends away from said second groove, wherein a valley is formed between said first and second ramps.

4. A medical device according to claim 3, wherein:
said valley is of substantially constant diameter.

5. A medical device according to claim 3, wherein:
said second groove is located substantially adjacent and between said first gripping flange and said second ramp, and said second groove comprises a third ramp, said third ramp of increasing diameter as it extends toward said second ramp.

6. A medical device according to claim 3, wherein:
said at least one inwardly protrusion comprises at least two protrusions axially removed along the longitudinal axis of said outer shield member, wherein the first of said protrusions is adapted to engage said first groove in a locking fashion, and the second protrusion is adapted to engage said second groove in a disengageable fashion.

7. A medical device according to claim 6, wherein:
said at least two protrusions comprises two substantially circumferential protrusions.

8. A medical device according to claim 6, wherein:
said inner tube member further comprises a front end wall having an annular opening and a hollow neck portion supported by said front end wall, said hollow neck portion extending at least a short distance forward of said front end wall and having an opening adjacent said annular opening, said neck portion including outwardly extending locking means about an outer surface of said hollow neck portion, and said shield member further comprises a front end wall and a nozzle supported by said shield member front end wall, said nozzle and said shield member front end wall having openings for permitting the hollow needle to pass therethrough, and said nozzle having inwardly extending locking means located about the inner surface of said nozzle and adapted to lock with said outwardly extending locking means to prevent rotational movement of said shield member relative to said tube member when said shield member is in said retracted position.

9. A medical device according to claim 1, wherein: said at least one inwardly protrusion comprises at least two protrusions axially removed along the longitudinal axis of said outer shield member, wherein the first of said protrusions is adapted to engage said first groove in a locking fashion, and the second protrusion is adapted to engage said second groove in a disengageable fashion.

10. A medical device according to claim 9, wherein: said at least two protrusions comprises two substantially circumferential protrusions.

11. A medical device according to claim 10, wherein: said inner tube member comprises a third groove proximate to said first groove, said first and third grooves being separated by a distance approximately equal to the distance separating said first and second substantially circumferential protrusions, wherein said first groove is wider than said third groove, the first of said circumferential protrusions which is located forward of the second of said circumferential protrusions is of greater axial thickness than said second circumferential protrusion such that said first circumferential protrusion is arranged to lockingly engage said first groove but not said third groove.

12. A medical device according to claim 1, wherein: said inner tube member further comprises a front end wall having an annular opening and a hollow neck portion supported by said front end wall, said hollow neck portion extending at least a short distance forward of said front end wall and having an opening adjacent said annular opening, said neck portion including outwardly extending locking means about an outer surface of said hollow neck portion, and said shield member further comprises a front end wall and a nozzle supported by said shield member front end wall, said nozzle and said shield member front end wall having openings for permitting the hollow needle to pass therethrough, and said nozzle having inwardly extending locking means located about the inner surface of said nozzle and adapted to lock with said outwardly extending locking means to prevent rotational movement of said shield member relative to said tube member when said shield member is in said retracted position.

13. A medical device according to claim 1, wherein: said at least one outwardly extending second gripping flange comprises at least one ramped gripping flange, said at least one ramped gripping flange increasing in diameter as it extends toward the forward end of said shield member, said at least one ramped gripping flange arranged to be engaged and pushed by a thumb of a practitioner.

14. A medical device according to claim 13, wherein: said at least one ramped gripping flange is located at other than the extreme rear end and extreme forward end of said shield member and comprises at least one ramped gripping flange circumferentially located around said shield member.

15. A medical device according to claim 1, wherein: said at least one outwardly extending second gripping flange comprises at least one safety gripping flange arranged with a back face adapted for gripping between a thumb and a forefinger of a practitioner.

16. A medical device according to claim 15, wherein: said at least one safety gripping flange is located at the forward end of said shield member and comprises at least one outwardly extending gripping flange circumferentially located around said shield member.

17. A medical device according to claim 1, wherein: said at least one outwardly extending second gripping flange comprises at least one ramped gripping flange and at least one safety gripping flange, said at least one ramped gripping flange increasing in diameter as it extends toward the forward end of said shield member and arranged to be engaged and pushed by a thumb of a practitioner, and said at least one safety gripping flange arranged with a back face adapted for gripping between a thumb and a forefinger of a practitioner.

18. A medical device according to claim 17, wherein: said outer surface of said inner tube member includes a first ramp substantially rearwardly adjacent said first groove, said first ramp being of decreasing diameter as it extends away from said first groove, and a second ramp substantially forwardly adjacent said second groove, said second ramp being of decreasing diameter as it extends away from said second groove, wherein a valley is formed between said first and second ramps.

19. A medical device according to claim 18, wherein: said at least one inwardly protrusion comprises at least two substantially circumferential protrusions axially removed along the longitudinal axis of said outer shield, wherein the first of said protrusions is adapted to engage said first groove in a locking fashion, and the second protrusion is adapted to engage said second groove in a disengageable fashion.

20. A medical device according to claim 19, wherein: said inner tube member comprises a third groove proximate to said first groove, said first and third grooves being separated by a distance approximately equal to the distance separating said first and second substantially circumferential protrusions, wherein said first groove is wider than said third groove, the first of said circumferential protrusions which is located forward of the second of said circumferential protrusions is of greater axial thickness than said second circumferential protrusion such that said first circumferential protrusion is arranged to lockingly engage said first groove but not said third groove.

21. A medical device according to claim 1, wherein: said inner tube member and hollow outer shield member are injection moldings of plastic mixed with a lubricant.

22. A medical device according to claim 21, wherein: said plastic is polypropylene, and said lubricant is a nitrogenous aliphatic compound.

23. A medical device according to claim 1, wherein: said shoulder extends along an axis parallel to the longitudinal axis of said outer shield member, and said shoulder is of substantially non-decreasing diameter as it extends away from said first groove.

24. A medical device for assembly with a hollow needle and for use by a medical practitioner, comprising:
a) an inner tube member having a substantially cylindrical inner surface, a front end having receiving means for having the hollow needle secured thereto, an open rear end, first gripping means substantially at said open rear end, and an outer surface having engaging means and a first locking means, said first locking means comprising a first circumferential groove in said outer surface and towards said front end of said inner tube member, a front shoulder on said outer surface adjacently forward of said first groove, and a first ramp on said outer surface adjacently rearward of said first groove, said first ramp decreasing in diameter as it extends away from said first groove, and said shoulder being slightly larger in diameter than said first ramp adjacently rearward of said first groove;

b) a hollow outer shield member having a substantially cylindrical outer surface having second gripping means, and an inner surface having at least one second locking means, a front end having an opening therein, and a substantially open rear end, wherein in a first retracted position, said at least one second locking means engages said engaging means, said engaging means for disengagingly engaging said at least one second locking means, and in a second extended and locked position, said at least one second locking means locks with said first locking means and said hollow outer shield member shields the needle, said first locking means for lockingly engaging said at least one second locking means, and said first gripping means, said second gripping means, said outer surface of said inner tube member, and said inner surface of said hollow outer shield member constitute means for allowing one handed manipulation by the medical practitioner of said medical device such that said outer shield member is moved from said first retracted position to said second extended and locked position through use of only one hand of the medical practitioner.

25. A medical device according to claim 24, wherein:
said at least one second locking means comprises at least one inwardly extending protrusion extending from said inner surface of said outer shield member, said at least one inwardly extending portrusion sized to engage said engagement means and to engage and lock with said first groove.

26. A medical device according to claim 25, wherein:
said at least one inwardly extending protrusion comprises two substantially circumferential protrusions, the first of said two substantially circumferential protrusions located forward of the second and used to engage and lock with said first groove, and the second of said two substantially circumferential protrusions used to disengagingly engage said engagement means.

27. A medical device according to claim 26, wherein:
said outer surface of said inner tube member further includes a first anti-rotational locking means and said inner surface of said outer shield member further includes a second anti-rotational locking means, said first anti-rotational locking means for engaging said second anti-rotational locking means and preventing rotation of said inner tube member relative to said outer shield member when said inner tube member and outer shield member are in said first retracted position.

28. A medical device according to claim 25, wherein:
said engagement means comprises a second circumferential groove in said outer surface and towards said rear end of said inner tube member.

29. A medical device according to claim 28, wherein:
said engagement means further comprises a second ramp increasing in diameter as it extends from said second circumferential groove toward said front end of said inner tube member.

30. A medical device according to claim 29, wherein:
said outer surface of said inner tube member further includes a third ramp forwardly adjacent said second ramp and decreasing in diameter as it extends from said second ramp towards said front end of said inner tube, and a valley between said first and third ramps of reduced diameter relative to the diameter circumscribed by said at least one inwardly extending protrusion to permit said inwardly extending protrusion to slide thereover.

31. A medical device according to claim 30, wherein:
said inner tube member and said outer shield member are injection moldings of plastic mixed with a lubricant.

32. A medical device for assembly with a hollow needle and for use by a medical practitioner, comprising:
a) an inner tube member having a substantially cylindrical inner surface, a front end having receiving means for having the hollow needle secured thereto, an open rear end, first gripping means substantially at said open rear end, and an outer surface having engaging means and a first locking means;

b) a hollow outer shield member having a substantially cylindrical outer surface having second gripping means, and an inner surface having at least one second locking means, a front end having an opening therein, and a substantially open rear end, wherein in a first retracted position, said at least one second locking means engages said engaging means, said engaging means for disengagingly engaging said at least one second locking means, and in a second extended and locked position, said at least one second locking means locks with said first locking means and said hollow outer shield member shields the needle, said first locking means for lockingly engaging said at least one second locking means, said first gripping means, said second gripping means, said outer surface of said inner tube member, and said inner surface of said hollow outer shield member constitute means for allowing one handed manipulation by the medical practitioner of said medical device such that said outer shield member is moved from said first retracted position to said second extended and locked position through use of only one hand of the medical practitioner, and said inner tube member and said outer shield member are injection moldings of plastic mixed with a lubricant.

33. A medical device according to claim 32, wherein:
said first locking means comprises a first circumferential groove in said outer surface and towards said front end of said inner tube member, a front shoulder on said outer surface adjacently forward of said first groove, and a first ramp on said outer surface adjacently rearward of said first groove, said first ramp decreasing in diameter as it extends away from said first groove, and said shoulder being slightly larger in diameter than said first ramp adjacently rearward of said first groove.

34. A medical device according to claim 33, wherein:

said at least one second locking means comprises at least one inwardly extending protrusion extending from said inner surface of said outer shield member, said at least one inwardly extending protrusion sized to engage said engagement means and to engage and lock with said first groove.

35. A medical device according to claim 34, wherein: said at least one inwardly extending protrusion comprises two substantially circumferential protrusions, the first of said two substantially circumferential protrusions located forward of the second and used to engage and lock with said first groove, and the second of said two substantially circumferential protrusions used to disengagingly engage said engagement means.

36. A medical device according to claim 35, wherein: said outer surface of said inner tube member further includes a first anti-rotational locking means and said inner surface of said outer shield member further includes a second anti-rotational locking means, said first anti-rotational locking means for engaging said second anti-rotational locking means and preventing rotation of said inner tube member relative to said outer shield member when said inner tube member and outer shield member are in said first retracted position.

37. A medical device according to claim 34, wherein: said engagement means comprises a second circumferential groove in said outer surface and towards said rear end of said inner tube member.

38. A medical device according to claim 37, wherein: said engagement means further comprises a second ramp increasing in diameter as it extends from said second circumferential groove toward said front end of said inner tube member.

* * * * *